United States Patent
Narita (10) Patent No.: US 11,683,436 B2
(45) Date of Patent: Jun. 20, 2023

(54) SYSTEM THAT APPROPRIATELY SYNTHESIZES OUTPUT DATA AND CODE PROVIDED BY EXTERNAL SETTLEMENT SERVICE, CONTROL METHOD FOR SYSTEM, AND STORAGE MEDIUM

(71) Applicant: CANON KABUSHIKI KAISHA, Tokyo (JP)

(72) Inventor: Tateki Narita, Tokyo (JP)

(73) Assignee: CANON KABUSHIKI KAISHA, Tokyo (JP)

(*) Notice: Subject to any disclaimer, the term of this patent is extended or adjusted under 35 U.S.C. 154(b) by 0 days.

(21) Appl. No.: 17/480,015

(22) Filed: Sep. 20, 2021

(65) Prior Publication Data

US 2022/0124218 A1 Apr. 21, 2022

(30) Foreign Application Priority Data

Oct. 15, 2020 (JP) .............................. JP2020-174021

(51) Int. Cl.
| | | |
|---|---|---|
| *H04N 1/00* | (2006.01) | |
| *H04N 1/34* | (2006.01) | |
| *G16H 15/00* | (2018.01) | |
| *G16H 10/60* | (2018.01) | |

(52) U.S. Cl.
CPC ............. *H04N 1/34* (2013.01); *G16H 10/60* (2018.01); *G16H 15/00* (2018.01); *H04N 1/00214* (2013.01); *H04N 1/00334* (2013.01)

(58) Field of Classification Search
CPC ........................................................ H04N 1/34
See application file for complete search history.

(56) References Cited

U.S. PATENT DOCUMENTS

| | | | |
|---|---|---|---|
| 2007/0211288 A1* | 9/2007 | Uejo ................... | H04N 1/32122 |
| | | | 358/1.16 |
| 2013/0179336 A1* | 7/2013 | Lyons ................. | G06Q 20/3276 |
| | | | 705/39 |
| 2017/0116590 A1* | 4/2017 | Ozawa .................. | G06Q 20/102 |
| 2017/0132633 A1* | 5/2017 | Whitehouse ............ | H04L 63/08 |
| 2017/0372287 A1* | 12/2017 | Matsuo .................. | G06Q 40/12 |
| 2020/0167622 A1* | 5/2020 | Sinha .................. | G06Q 20/405 |
| 2020/0286062 A1* | 9/2020 | Narita .................. | G06Q 20/209 |
| 2021/0157531 A1* | 5/2021 | Matsuzawa ........... | G06Q 20/209 |
| 2022/0084004 A1* | 3/2022 | Takemura .............. | G07G 1/06 |

FOREIGN PATENT DOCUMENTS

JP 2007-129586 A 5/2007

* cited by examiner

*Primary Examiner* — Benjamin O Dulaney
(74) *Attorney, Agent, or Firm* — Venable LLP (57) ABSTRACT

A system that appropriately synthesizes output data and a code provided by an external settlement service is provided. The system comprising a transmitting unit configured to transmit information for generating a code used for paying a amount of money to an external settlement service, a receiving unit configured to receive the code generated based on the information transmitted by the transmitting unit, and a synthesizing unit configured to synthesize the code received by the receiving unit and output data.

7 Claims, 10 Drawing Sheets

SYSTEM THAT APPROPRIATELY SYNTHESIZES OUTPUT DATA AND CODE PROVIDED BY EXTERNAL SETTLEMENT SERVICE, CONTROL METHOD FOR SYSTEM, AND STORAGE MEDIUM

BACKGROUND OF THE INVENTION

Field of the Invention

The present invention relates to a system, a control method for the system, and a storage medium.

Description of the Related Art

In payments at retail stores and counter payments in various types of businesses, in order to improve operational efficiencies of business operators and the convenience of customers, the introduction of a cashless payment, which uses a settlement code such as a two-dimensional code, has been promoted. However, in some types of businesses such as medical institutions, despite a demand for improving the efficiency and convenience of the counter payment, the cashless payment is not widespread due to reasons such as a cost burden, etc.

In the cashless payment that uses the settlement code, there are a store scanning method, in which the business operator scans the settlement code displayed by a user on a smartphone or the like, and a user scanning method, in which the user scans the settlement code presented by the business operator by using the smartphone or the like. The user scanning method has an advantage that the business operator does not need to prepare a scanning device, the cost burden is suppressed, and it is easy to introduce. Further, in the user scanning method, since by using the settlement code that includes information about the amount of money, it is not necessary to input the amount of money, as a result, it is possible to improve the efficiency and convenience of the counter payment. It is being considered to introduce a cashless payment that uses the user scanning method having such a feature into payments of the medical institutions. For example, by attaching an image of the settlement code that includes information about billed amount of money to medical receipts (hereinafter, simply referred to as "receipts") such as health insurance claims of medical fees and dispensing fees, which are printed at the time of paying in the medical institution, it is possible to improve the efficiency and convenience of the counter payment of the medical institution while suppressing the cost burden. As techniques related to attaching a code image to a printed matter in this way, a technique disclosed in Japanese Laid-Open Patent Publication (kokai) No. 2007-129586 has been proposed. In Japanese Laid-Open Patent Publication (kokai) No. 2007-129586, a printing device generates a code pattern such as a QR code (registered trademark) based on personal information of a user who has logged in to the printing device, and synthesizes the generated code pattern and data to be printed.

However, the settlement code (i.e., the code pattern) used in the cashless payment is generated not by the printing device that prints print data (i.e., the data to be printed), but by an external settlement service that provides a payment service based on the settlement code. Therefore, in order to synthesize the intended settlement code with the print data, there is a strong demand for a mechanism capable of appropriately associating the print data with the settlement code provided by the external settlement service.

SUMMARY OF THE INVENTION

The present invention provides a system that appropriately synthesizes output data and a code provided by an external settlement service, a control method for the system, and a storage medium.

Accordingly, the present invention provides a system comprising a transmitting unit configured to transmit information for generating a code used for paying a amount of money to an external settlement service, a receiving unit configured to receive the code generated based on the information transmitted by the transmitting unit, and a synthesizing unit configured to synthesize the code received by the receiving unit and output data.

According to the present invention, it is possible to appropriately associate the output data with the code provided by the external settlement service.

Further features of the present invention will become apparent from the following description of exemplary embodiments with reference to the attached drawings.

DESCRIPTION OF THE EMBODIMENTS

The present invention will now be described in detail below with reference to the accompanying drawings showing embodiments thereof.

At first, an image forming apparatus and an information processing apparatus, which constitute a system according to a first embodiment of the present invention, will be described.

Figure 1A:
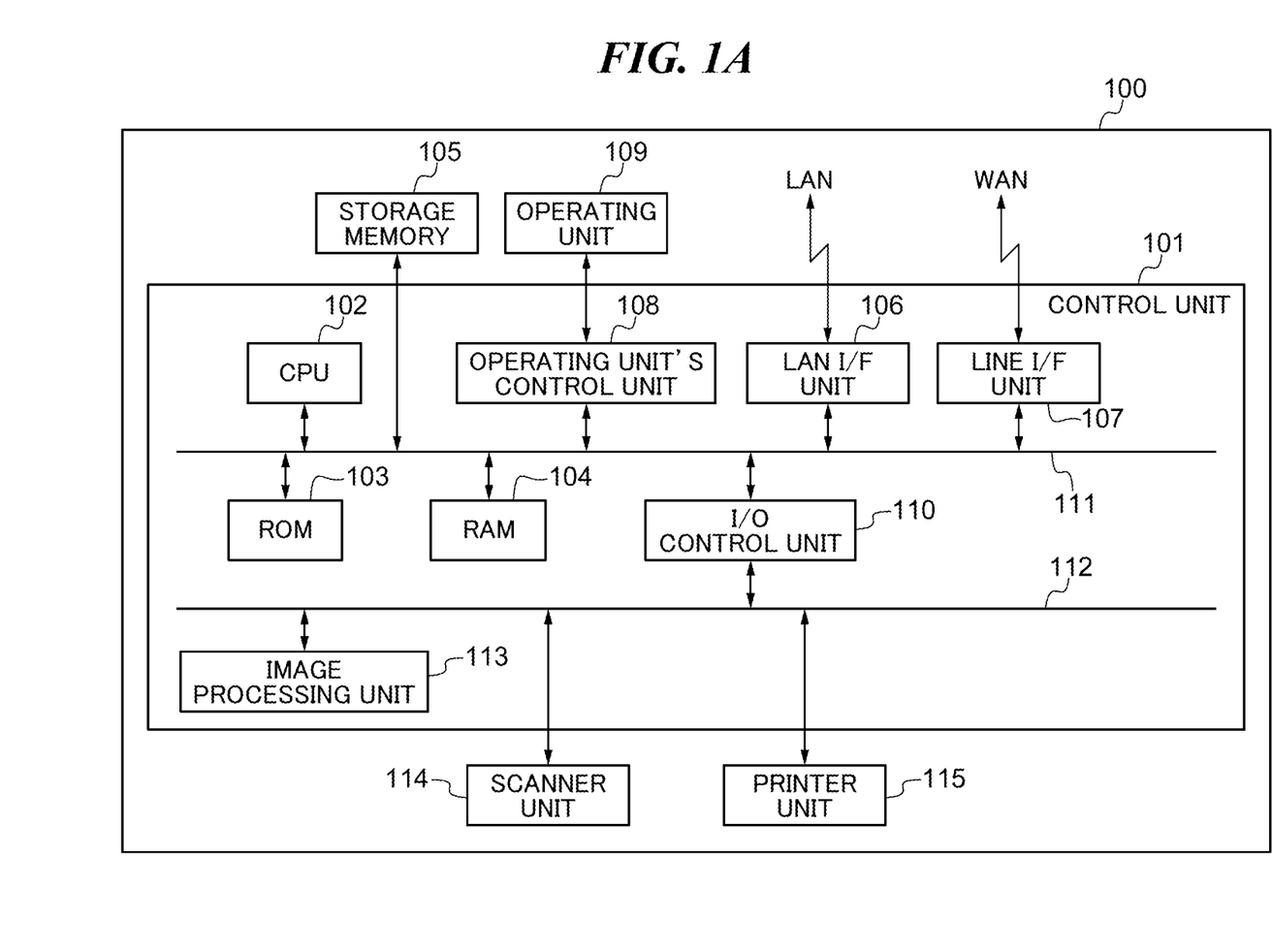
FIGS. 1A and 1B are diagrams that schematically show configurations of an image forming apparatus and an information processing apparatus, which constitute a system according to an embodiment of the present invention.
Figure 1B:
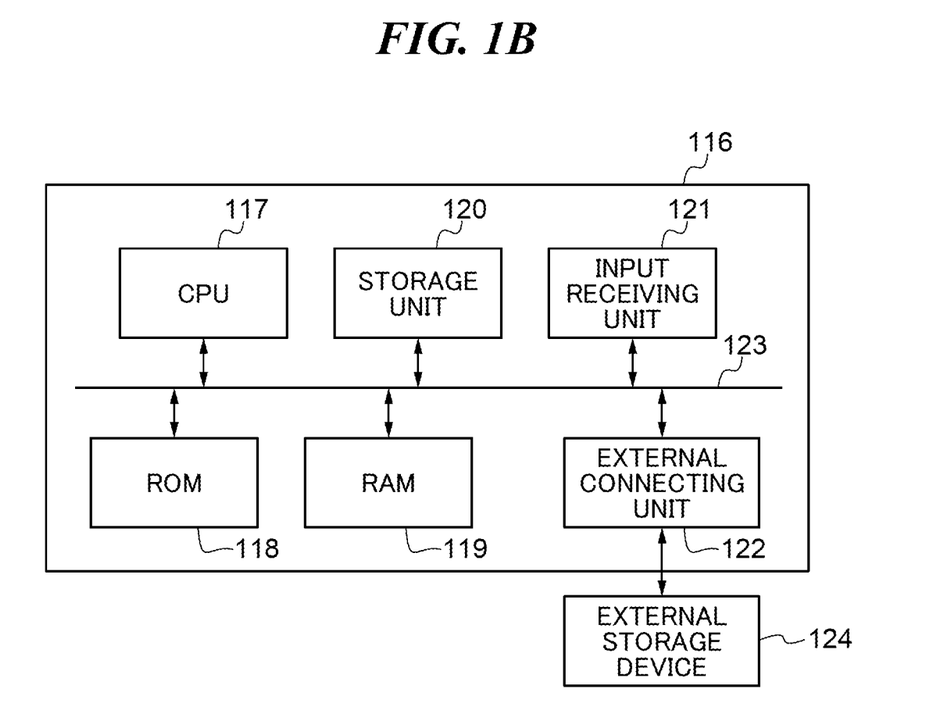

FIGS. 1A and 1B are diagrams that schematically show configurations of an image forming apparatus 100 and an information processing apparatus 116, which constitute a system according to an embodiment of the present invention. FIG. 1A shows the configuration of the image forming apparatus 100. Further, FIG. 1B shows the configuration of the information processing apparatus 116.

As shown in FIG. 1A, the image forming apparatus 100 has a control unit 101, a storage memory 105, an operating unit 109, a scanner unit 114, and a printer unit 115. The control unit 101 is connected to the storage memory 105, the operating unit 109, the scanner unit 114, and the printer unit 115, respectively. Further, the control unit 101 has a CPU (Central Processing Unit) 102, a ROM (Read Only Memory) 103, a RAM (Random Access Memory) 104, a LAN (Local Area Network) I/F (interface) unit 106, a line I/F unit 107, an operating unit's control unit 108, an I/O (Input/Output) control unit 110, and an image processing unit 113. The CPU 102, the ROM 103, the RAM 104, the LAN I/F unit 106, the line I/F unit 107, the operating unit's control unit 108, and the I/O control unit 110 are connected to each other via a system bus 111. Furthermore, the image processing unit 113 is connected to the I/O control unit 110 via an image bus 112.

The control unit 101 comprehensively controls the entire image forming apparatus 100. The CPU 102 executes a program stored in the ROM 103 or the storage memory 105 to cause a software module (not shown) of the image forming apparatus 100 to execute each processing. The ROM 103 stores boot programs of the system, etc. The RAM 104 is a system working memory area for the CPU 102 to execute the software module (not shown) of the image forming apparatus 100. Further, the RAM 104 is an image memory for temporarily storing image data when performing a processing with respect to the said image data. The storage memory 105 is configured by an HDD (Hard Disk Drive) or an SSD (Solid State Drive), and is used as an internal storage. For example, a system software module for realizing various functions of the image forming apparatus 100 and the image data transferred from the RAM 104 are stored in the storage memory 105.

The LAN I/F unit 106 is an I/F for connecting the image forming apparatus 100 to a LAN. The LAN OF unit 106 performs data communications with an external apparatus connected to the LAN, for example, the information processing apparatus 116 or an external storage device 124 that retains a payment data set, which will be described later. Further, the line I/F unit 107 is an I/F for connecting the image forming apparatus 100 to a WAN (Wide Area Network). The line I/F unit 107 performs data communications with the external apparatus connected to the WAN. Furthermore, the operating unit's control unit 108 is an I/F of the control unit 101 and the operating unit 109. For example, the operating unit's control unit 108 outputs a VGA (Video Graphics Array) signal to the operating unit 109, and causes the operating unit 109 to display an image corresponding to the VGA signal. Further, the operating unit's control unit 108 outputs information, which is inputted into the operating unit 109 by the user, to the CPU 102. The operating unit 109 is equipped with a display device, a keypad device and a card reader device, and is configured by an LCD (Liquid Crystal Display) touch panel and the like. The operating unit 109 interprets the VGA signal outputted from the operating unit's control unit 108 and displays the image corresponding to the VGA signal.

The I/O control unit 110 is a bus bridge that connects the system bus 111 and the image bus 112, and converts a data structure of the system bus 111. The image bus 112 is configured by a general-purpose bus such as a PCI (Peripheral Component Interconnect) bus, IEEE1394, and PCIEx (Peripheral Component Interconnect Express), and transfers the image data at high speed. The I/O control unit 110, the image processing unit 113, the scanner unit 114, and the printer unit 115 are connected to the image bus 112. The image bus 112 performs a synchronous/asynchronous conversion of the image data. The image processing unit 113 is configured by a plurality of ASICs (Application Specific Integrated Circuits). The image processing unit 113 performs a resolution conversion processing, a compression processing, a decompression processing, a binary image/multi-level image conversion processing, etc. with respect to the image data. The scanner unit 114 reads a document and generates image data. The printer unit 115 prints the image data generated by the scanner unit 114 and print data, which is data to be printed and is obtained from the information processing apparatus 116.

As shown in FIG. 1B, the information processing apparatus 116 has a CPU 117, a ROM 118, a RAM 119, a storage unit 120, an input receiving unit 121, and an external connecting unit 122. The CPU 117, the ROM 118, the RAM 119, the storage unit 120, the input receiving unit 121, and the external connecting unit 122 are connected to each other via a system bus 123.

The CPU 117 executes a program stored in the ROM 118 to cause a software module (not shown) of the information processing apparatus 116 to execute each processing. The ROM 118 stores boot programs of the system, etc. The RAM 119 is a system working memory area for the CPU 117 to execute the software module (not shown) of the information processing apparatus 116. Further, the RAM 119 is a memory for temporarily storing data when performing a processing with respect to the said data. The storage unit 120 is a non-volatile storage device for storing the image data and setting information, and is, for example, the HDD or the SSD. The input receiving unit 121 is an input device such as a keyboard or a touch screen. The user inputs various instructions, setting values, etc. into the input receiving unit 121. The external connecting unit 122 performs data communications with the external apparatus or an external system via the LAN, the Internet, or the like.

By the way, in the payments at the retail stores and the counter payments in various types of businesses, in order to improve the operational efficiencies of the business operators and the convenience of the customers, the introduction of the cashless payment, which uses the settlement code (the code pattern) such as the two-dimensional code, has been promoted. However, in some types of businesses such as the medical institutions, despite the demand for improving the efficiency and convenience of the counter payment, the cashless payment is not widespread due to reasons such as the cost burden, etc., and payments by cash are being made.

Figure 2:
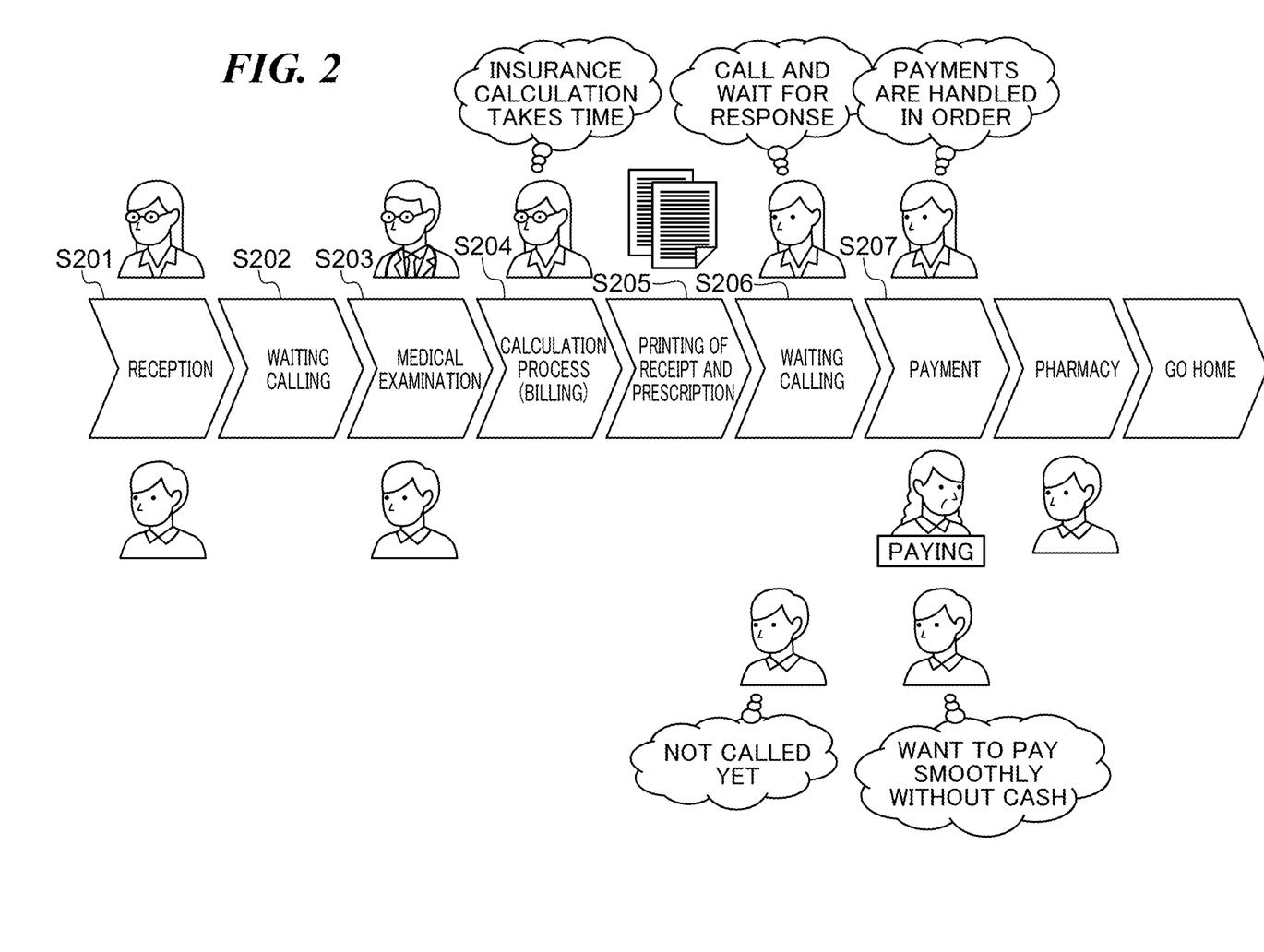
FIG. 2 is a figure that shows a flow of payment by cash in a medical institution.

FIG. 2 is a figure that shows a flow of the payment by cash in the medical institution. Moreover, in the present embodiment, a hospital will be described as an example of the medical institution, but the medical institution is not limited to the hospital and may be a pharmacy or the like.

In the medical institution, as shown in FIG. 2, after a reception process (a step S201), a waiting/calling (a step S202), and a medical examination (a step S203) are performed, a patient becomes in a payment waiting state. On the other hand, a clerical worker of the medical institution (hereinafter, simply referred to as "a clerical worker") performs a calculation process (billing) of the receipts necessary for the counter payment (a step S204), and performs printing of the receipts and prescriptions (a step S205). After completing the printing of the receipts and the prescriptions, the clerical worker calls the patients waiting for payment (a step S206), and performs a payment process of the called patients (a step S207). In the step S207, since the payment is made in cash, it takes time to process the payment of each of the called patients, and waiting in order occurs. For this reason, in the case of the payment by cash, the work efficiency of the clerical worker of the medical institution is poor, and patient's waiting time for the payment process has increased. Responding to such a situation, in the payment of the medical institution, the introduction of payment by a settlement code, which uses the external settlement service, is being considered. For example, by attaching the settlement code that includes the information about billed amount of money to the receipts, which are printed at the time of paying in the medical institution, it is possible to improve the efficiency and convenience of the counter payment of the medical institution. In order to realize such a cashless payment, it is necessary to synthesize the settlement code, which is provided by the external settlement service, and print data of the receipts. In order to synthesize the intended settlement code with the print data of the receipts, there is the strong demand for the mechanism capable of appropriately associating the print data of the receipts with the settlement code provided by the external settlement service.

Responding to this strong demand, in the present embodiment, a settlement code for settling the amount of money, which is inputted together when inputting a patient registration card ID (identification), is obtained from the external settlement service, and the said settlement code and the print data, which is designated together when inputting the patient registration card ID, are associated with the patient registration card ID and then are stored.

Figure 3:
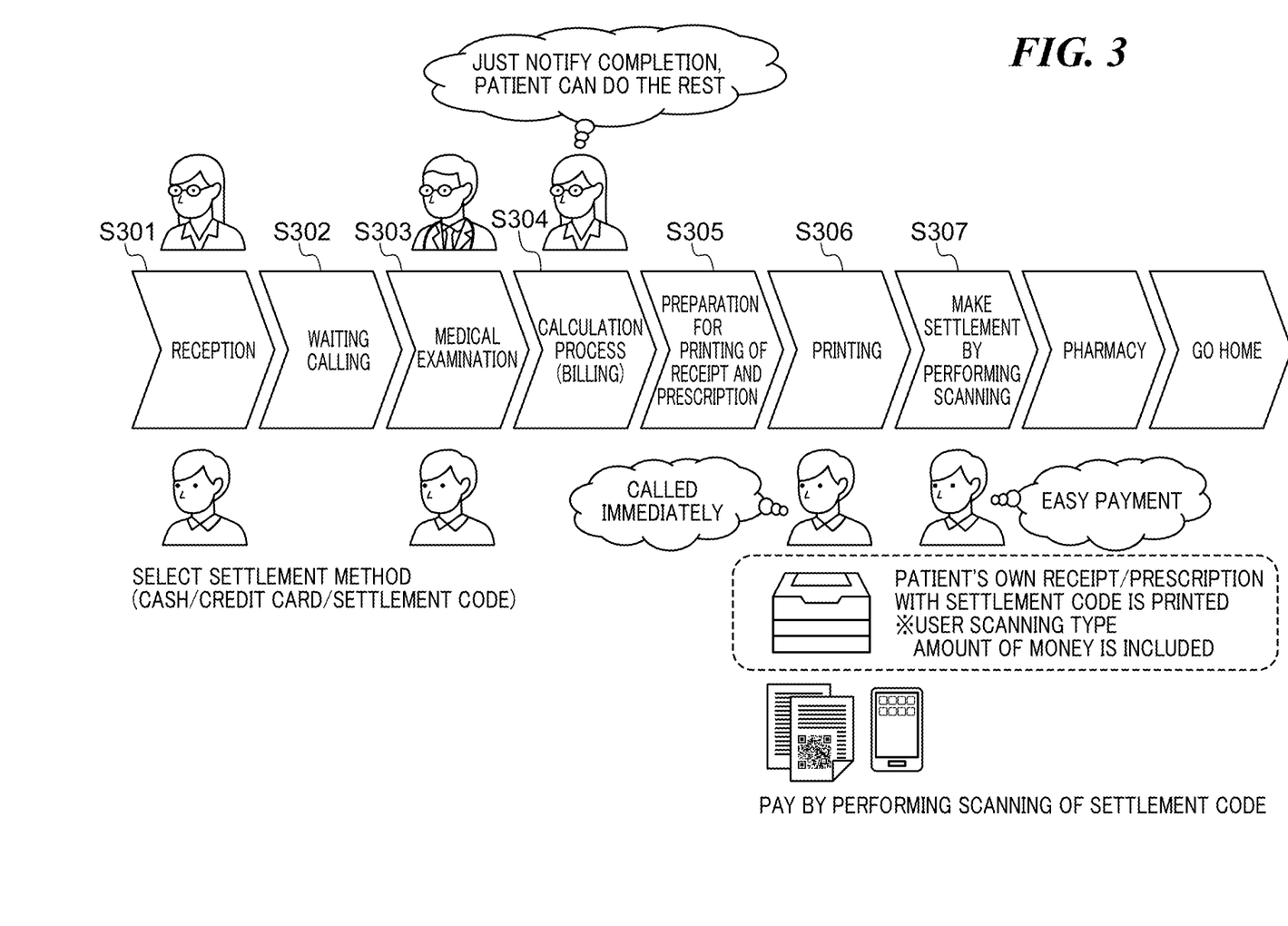
FIG. 3 is a figure that shows a flow of payment by a settlement code in a first embodiment.

FIG. 3 is a figure that shows a flow of the payment by the settlement code in the first embodiment. As shown in FIG. 3, the patient performs a reception process (a step S301). In the step S301, the patient selects "settlement code" from "cash", "credit card" and "settlement code" as a settlement method. At this time, the patient selects one external settlement service from a plurality of external settlement services that provide the payment service based on the settlement code. After that, steps S302 to S304, which are the same processes as steps S202 to S204, are performed. After that, the clerical worker prepares for the printing of the receipts and the prescriptions (a step S305). In the step S305, the clerical worker does not perform the printing of the receipts and the prescriptions, but operates the information processing apparatus 116 to prepare the print data for performing the printing of the receipts and the prescriptions and the settlement code. Upon completion of these preparations, the clerical worker will notify the patient that the preparation is complete, i.e., the clerical worker will transmit a preparation completion notification to the patient. Moreover, details of the processing executed by the information processing apparatus 116 in the step S305 will be described later.

The patient who has received the preparation completion notification performs printing of the print data and the settlement code that are prepared by the clerical worker, by using the image forming apparatus 100 installed in the medical institution (a step S306). As a result, for example, the receipt including the settlement code is printed. The patient scans the printed settlement code by using patient's own smartphone and makes the payment through the external settlement service (a step S307). In this way, by making the payment by the settlement code, it is possible to prevent the occurrence of waiting in order of the payment process and decrease the patient's waiting time for the payment process. In addition, it is possible to reduce man-hours for the payment process and improve the work efficiency of the clerical worker.

Figure 4:
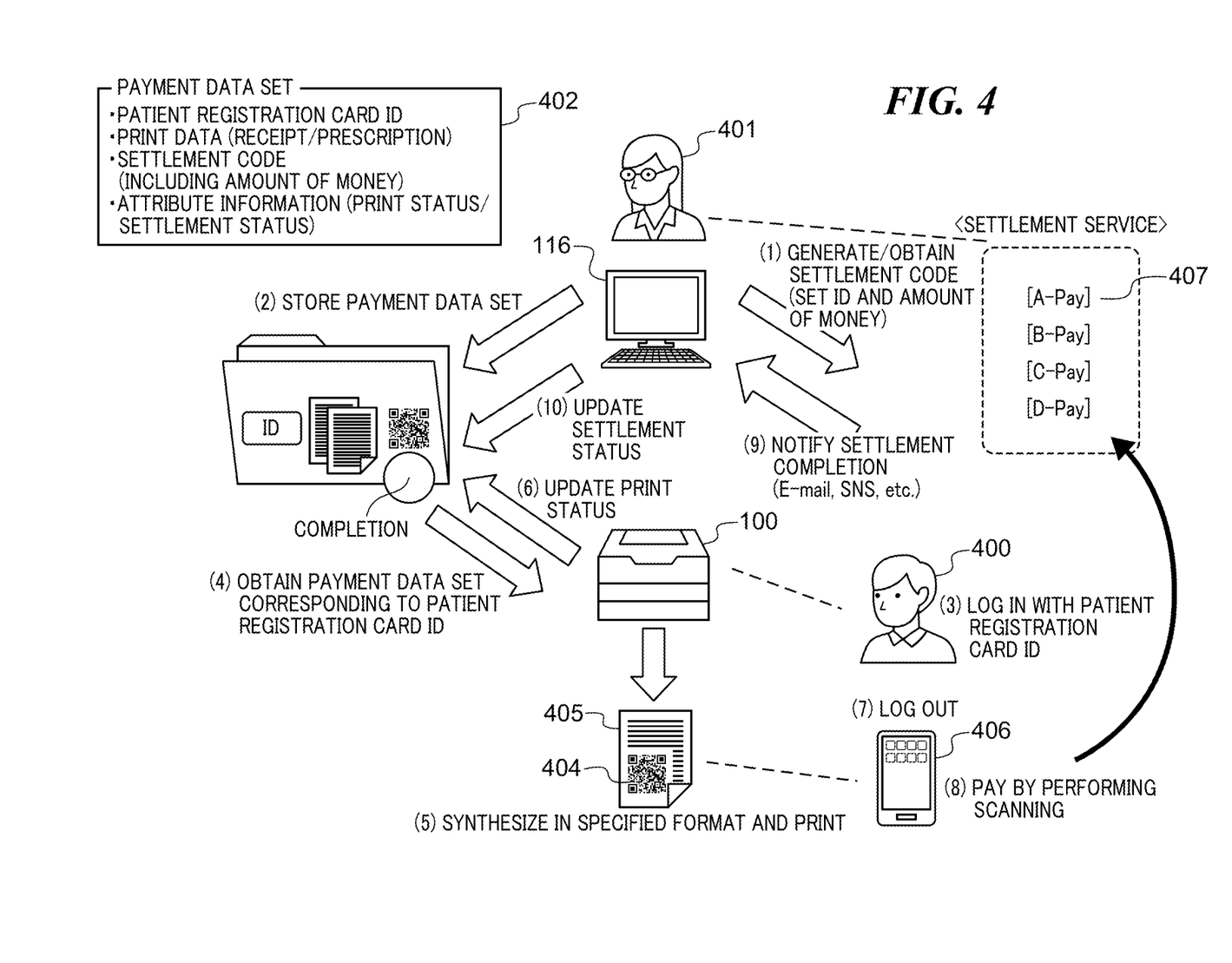
FIG. 4 is a figure for explaining detailed procedures of steps S305 to S307 of FIG. 3.

FIG. 4 is a figure for explaining detailed procedures of the steps S305 to S307 of FIG. 3. In the step S305 described above, the information processing apparatus 116 generates the print data for performing the printing of the receipts and the prescriptions of a patient 400 according to an instruction issued by a clerical worker 401, and also accesses to the external settlement service. At this time, the information processing apparatus 116 accesses to the external settlement service, which is selected together with the selected settlement method by the patient 400 in the step S301 from the plurality of external settlement services that provide the payment service based on the settlement code. The information processing apparatus 116 requests the external settlement service to generate a settlement code based on the patient registration card ID (user identification information) of the patient 400 and the amount of money that are inputted by the clerical worker 401 (see, for example, (1) in FIG. 4). When obtaining the settlement code generated according to this request from the external settlement service, the information processing apparatus 116, which functions as a storage control unit, stores a payment data set 402 that includes the patient registration card ID, the print data, the settlement code, and attribute information of the patient 400 (see, for example, (2) in FIG. 4). The attribute information in the payment data set 402 includes a print status and a settlement status. For example, as the print status, information indicating whether or not printing using the payment data set 402 has been executed is set in the attribute information. Further, as the settlement status of the attribute information, in the case that the settlement method is "settlement code", information indicating whether or not settlement using the payment data set 402 has been executed is set. In the case that the settlement method is not "settlement code", a non-settlement code, which indicates that it is not the payment by the settlement code, is set. The information processing apparatus 116 stores the payment data set 402 in a predetermined folder of a predetermined storage place. The predetermined storage place is, for example, the external storage device 124 capable of performing communications via the external connecting unit 122, or the storage unit 120 that functions as a storage unit. Upon completing the storage of the payment data set 402, the clerical worker 401 will transmit the preparation completion notification to the patient 400.

The patient 400 who has received the preparation completion notification inputs the patient registration card ID of the patient 400 into the operating unit 109 and logs in to the image forming apparatus 100 (see, for example, (3) in FIG. 4). The image forming apparatus 100, which has received a print instruction from the logged-in patient 400, obtains the payment data set 402 corresponding to the patient registration card ID inputted at the time of login from the above predetermined storage place (see, for example, (4) in FIG. 4). Next, the image forming apparatus 100 refers to the attribute information that is included in the obtained payment data set 402. For example, in the case that both the print status and the settlement status in this attribute information are "unexecuted", the image forming apparatus 100 synthesizes the settlement code with the print data by means of a specified format stored in the RAM 104. Further, the image forming apparatus 100 prints the print data, in which the settlement code is synthesized (see, for example, (5) in FIG. 4). As a result, for example, a receipt 405 including an image 404 of the settlement code is printed. The image forming apparatus 100, which has completed printing, updates the printing status of the attribute information in the payment data set 402 stored in the above predetermined storage place to "executed" (see, for example, (6) in FIG. 4). Next, the patient 400 logs out of the image forming apparatus 100 (see, for example, (7) in FIG. 4).

Further, the patient 400 scans the image 404 of the settlement code of the receipt 405 by using a smartphone 406, and accesses to the external settlement service selected in the step 301, for example, a A-Pay 407 of FIG. 4, to perform the settlement (see, for example, (8) in FIG. 4). When the settlement is completed, the A-Pay 407, which is the external settlement service, notifies the information processing apparatus 116, which has requested the generation of the settlement code for performing this settlement, of the completion of the settlement by a predetermined method such as an e-mail (electronic mail), SNS (Social Networking Service), or the like (see, for example, (9) in FIG. 4). That is, upon the completion of the settlement, the A-Pay 407 will transmit a settlement completion notification to the information processing apparatus 116. The information processing apparatus 116, which has received the preparation completion notification, updates the settlement status of the attribute information in the payment data set 402 stored in the above predetermined storage place to "executed" (see, for example, (10) in FIG. 4). Here, the information processing apparatus 116 stores the attribute information whose settlement status has been updated to "executed" in the above predetermined storage place, or requests the external storage device 124, which serves as the above predetermined storage place, to update the settlement status to "executed".

Figure 5:
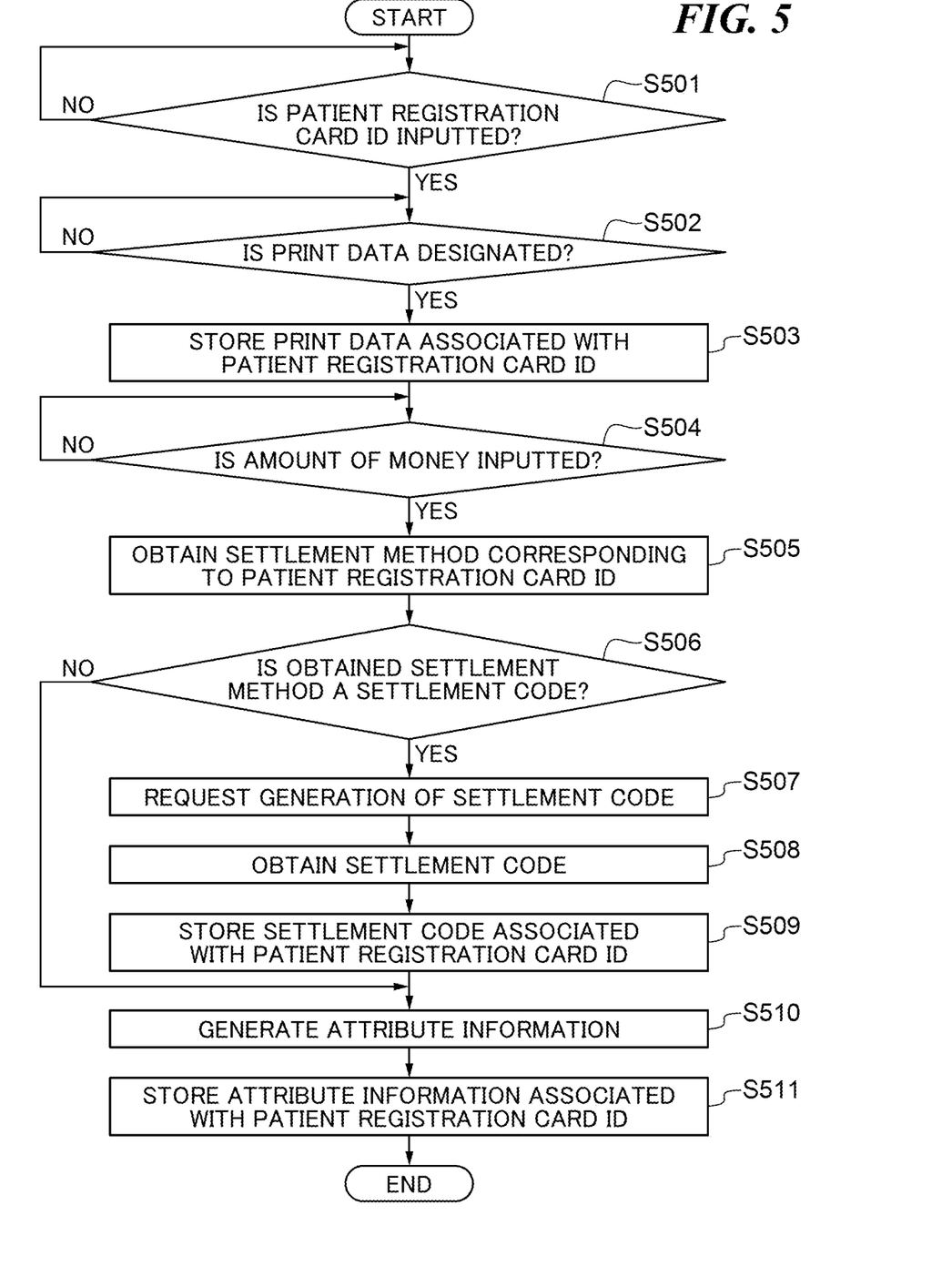
FIG. 5 is a flowchart that shows procedures of a payment data set storage processing executed by the information processing apparatus of FIG. 1B.

FIG. 5 is a flowchart that shows procedures of a payment data set storage processing executed by the information processing apparatus 116 of FIG. 1B. The processing of FIG. 5 is realized by the CPU 117 of the information processing apparatus 116 executing a program, which is read out from the ROM 118 and then is written into the RAM 119. Further, the processing of FIG. 5 is executed when the clerical worker prepares for the printing of the receipts and the prescriptions in the step S305.

As shown in FIG. 5, when the patient registration card ID of the patient is inputted into the input receiving unit 121 (YES in a step S501) and the print data is further designated (YES in a step S502), the CPU 117 performs the processing of a step S503. In the step S503, the CPU 117 associates the designated print data with the patient registration card ID, and then stores the designated print data associated with the patient registration card ID in the above predetermined storage place. Next, when the amount of money is inputted into the input receiving unit 121 (YES in a step S504), the CPU 117 obtains the settlement method corresponding to the above patient registration card ID from the storage unit 120 (a step S505). In the present embodiment, in the step S301, information, which indicates the settlement method and the external settlement service that are selected by the patient, is associated with the patient registration card ID of the said patient, and then is stored in the storage unit 120. Next, the CPU 117 judges whether or not the obtained settlement method is a settlement code (a step S506).

As a result of judging in the step S506, in the case that the obtained settlement method is not a settlement code, the payment data set storage processing proceeds to a step S510 that will be described later. As the result of the judging in the step S506, in the case that the obtained settlement method is a settlement code, the CPU 117 notifies the external settlement service selected by the patient in the step S301 of the amount of money inputted in the step S504. Further, the CPU 117, which functions as a request unit, requests the said external settlement service to generate a settlement code for settling the notified amount of money (a step S507).

When the CPU 117, which functions as an obtaining unit, obtains the settlement code for settling the above amount of money from the external settlement service as a response to this request (a step S508), the CPU 117 associates this settlement code with the patient registration card ID, and then stores this settlement code associated with the patient registration card ID in the above predetermined storage place together with the print data (a step S509). Next, the CPU 117 generates attribute information corresponding to the print data and the settlement code that are stored (a step S510). Next, the CPU 117 associates the attribute information with the patient registration card ID, and then stores the attribute information associated with the patient registration card ID in the above predetermined storage place together with the print data and the settlement code (a step S511). In this way, in the present embodiment, the payment data set that includes the print data, the settlement code, and the attribute information, which are associated with the patient registration card ID, is stored in the predetermined storage place. After that, the payment data set storage processing ends.

Figure 6:
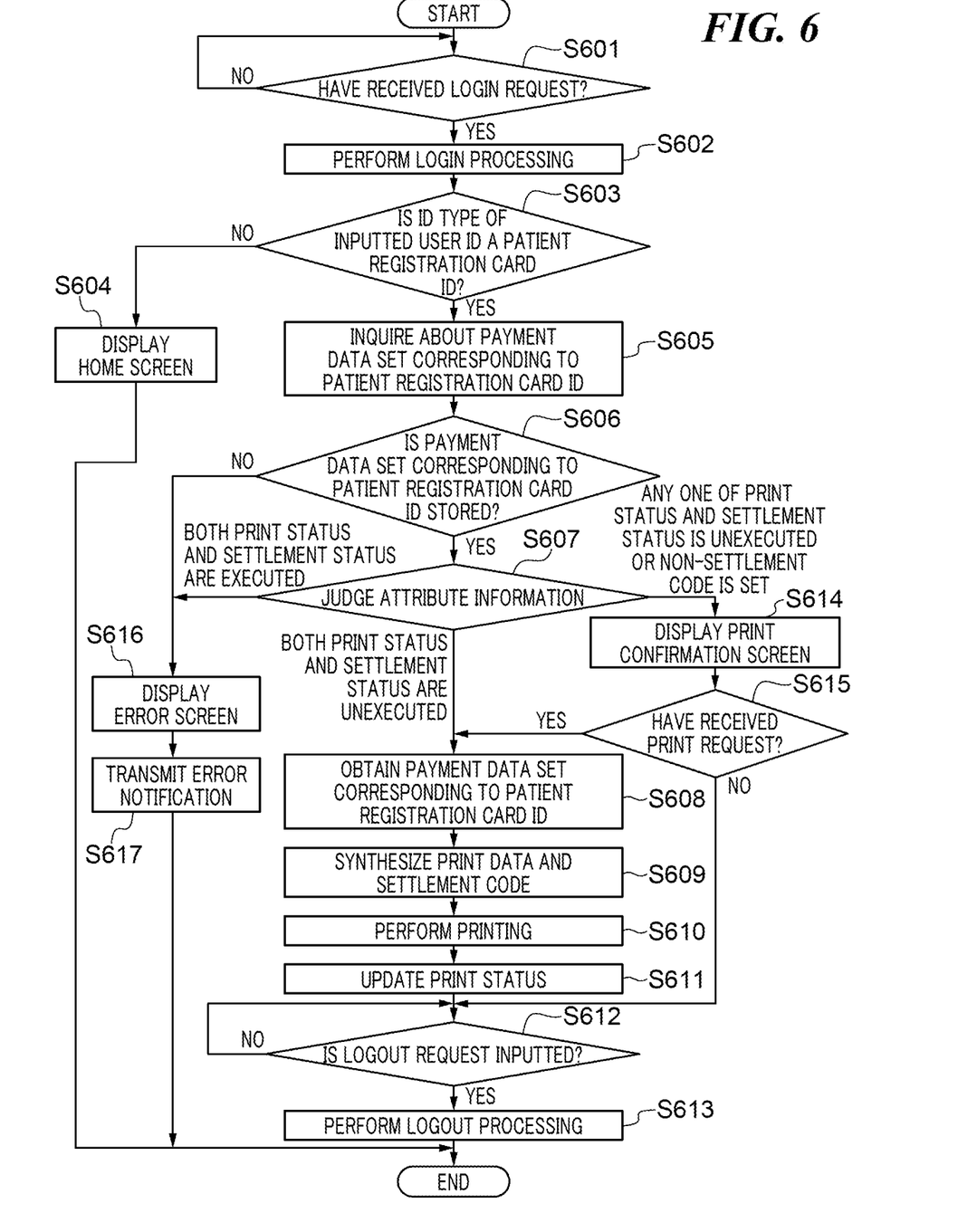
FIG. 6 is a flowchart that shows procedures of a print control processing executed by the image forming apparatus of FIG. 1A.

FIG. 6 is a flowchart that shows procedures of a print control processing executed by the image forming apparatus 100 of FIG. 1A. The processing of FIG. 6 is realized by the CPU 102 of the image forming apparatus 100 executing a program, which is read out from the ROM 103 or the storage memory 105 and then is written into the RAM 104. Further, the processing of FIG. 6 is executed when the patient performs the printing of the print data and the settlement code in the step S306.

As shown in FIG. 6, when a user ID is inputted into the operating unit 109 and a login request by this user ID has been received (YES in a step S601), the CPU 102, which functions as a login processing execution unit, performs a login processing based on the inputted user ID (a step S602). In the case that the authentication is successful, the user who has inputted the user ID into the operating unit 109 can give various instructions such as job execution to the image forming apparatus 100. Next, the CPU 102 judges whether or not an ID type of the inputted user ID is a patient registration card ID (a step S603).

As a result of judging in the step S603, in the case that the ID type of the inputted user ID is not a patient registration card ID, the CPU 102 displays a home screen on the operating unit 109 (a step S604), and the print control processing ends.

As the result of the judging in the step S603, in the case that the ID type of the inputted user ID is a patient registration card ID, the CPU 102 performs the processing of a step S605. In the step S605, the CPU 102 inquires of the external apparatus (the external storage device 124 or the information processing apparatus 116), which serves as the above predetermined storage place, about the payment data set corresponding to the patient registration card ID. The external apparatus transmits a response notification of this inquiry to the image forming apparatus 100. The response notification includes information, which indicates whether or not the payment data set corresponding to the patient registration card ID is stored in the external apparatus, and the attribute information in the payment data set corresponding to the patient registration card ID. The CPU 102 judges whether or not the payment data set corresponding to the patient registration card ID is stored in the external apparatus based on the response notification received from the external apparatus (a step S606).

As a result of judging in the step S606, in the case that the payment data set corresponding to the patient registration card ID is stored in the external apparatus, the CPU 102 judges the attribute information, which is included in the response notification received from the external apparatus (a step S607).

In the step S607, in the case that both the print status and the settlement status in the above attribute information are "unexecuted", the CPU 102, which functions as a data set obtaining unit, obtains the payment data set corresponding to the patient registration card ID from the external apparatus (a step S608). Next, the CPU 102, which functions as a synthesizing unit, obtains the print data and the settlement code from the payment data set, and synthesizes the settlement code with the said print data by means of the specified format stored in the RAM 104 (a step S609). Next, the CPU 102 controls the printer unit 115, which functions as a printing unit, to perform printing of the print data, in which the settlement code is synthesized (a step S610). When the printing is completed, the CPU 102 updates the printing status of the attribute information in the payment data set stored in the above predetermined storage place to "executed" (a step S611). In the step S611, the CPU 102 transmits the attribute information whose print status has been updated to "executed" to the external apparatus, which serves as the above predetermined storage place, or requests the external apparatus, which serves as the above predetermined storage place, to update the print status to "executed". Next, the CPU 102 waits until the user inputs a logout request into the operating unit 109. When the user inputs the logout request into the operating unit 109 (YES in a step S612), the CPU 102 performs a logout processing (a step S613), and the print control processing ends.

In the step S607, in the case that any one of the print status and the settlement status in the above attribute information is "unexecuted", or in the case that the non-settlement code is set in the said settlement status, the print control processing proceeds to a step S614. In the step S614, the CPU 102 displays a print confirmation screen (not shown), which confirms with the user about whether or not it is necessary to perform the printing, on the operating unit 109. Next, the CPU 102 judges whether or not a print request from the user has been received (a step S615).

As a result of judging in the step S615, in the case that the print request from the user has been received, the print control processing proceeds to the step S608. Further, as the result of the judging in the step S615, in the case that the print request from the user has not been received, the print control processing proceeds to the step S612.

In the step S607, in the case that both the print status and the settlement status in the above attribute information are "executed", the CPU 102 displays an error screen on the operating unit 109 (a step S616). Next, the CPU 102 transmits an error notification to a predetermined destination by an e-mail or the like (a step S617). As described above, in the present embodiment, it is determined whether or not to perform the printing using the payment data set based on the attribute information. After that, the print control processing ends.

According to the above-described embodiment, the settlement code for settling the amount of money, which is inputted together when inputting the patient registration card ID, is obtained from the external settlement service, and the said settlement code and the print data, which is designated together when inputting the patient registration card ID, are associated with the patient registration card ID and then are stored. As a result, it is possible to appropriately associate the print data with the settlement code provided by the external settlement service.

Further, in the above-described embodiment, the settlement code obtained from the external settlement service and the print data are stored in the storage unit 120 of the information processing apparatus 116. Thereby, in the configuration, in which the print data is outputted from the information processing apparatus 116 to the image forming apparatus 100, it is possible to appropriately associate the print data with the settlement code provided by the external settlement service.

Furthermore, in the above-described embodiment, the settlement code obtained from the external settlement service and the print data are stored in the external storage device 124. Thereby, in the configuration, in which the print data is outputted from the information processing apparatus 116 to the image forming apparatus 100 via the external storage device 124, it is possible to appropriately associate the print data with the settlement code provided by the external settlement service.

Moreover, in the above-described embodiment, the payment data set includes the attribute information that includes the print status and the settlement status, and it is determined whether or not to perform the printing based on the payment data set, on the basis of the attribute information included in the said payment data set. As a result, it is possible to prevent unnecessary printing such as printing of a receipt including a settlement code that has already been settled from being performed.

Next, an image forming apparatus and an information processing apparatus, which constitute a system according to a second embodiment of the present invention, will be described.

The configurations and effects of the second embodiment are basically the same as those of the first embodiment described above, and it differs from the first embodiment described above that in the second embodiment, the information processing apparatus 116 synthesizes the settlement code with the print data. Therefore, the descriptions of the duplicated configurations and effects will be omitted, and the different configurations and effects will be described below.

Figure 7:
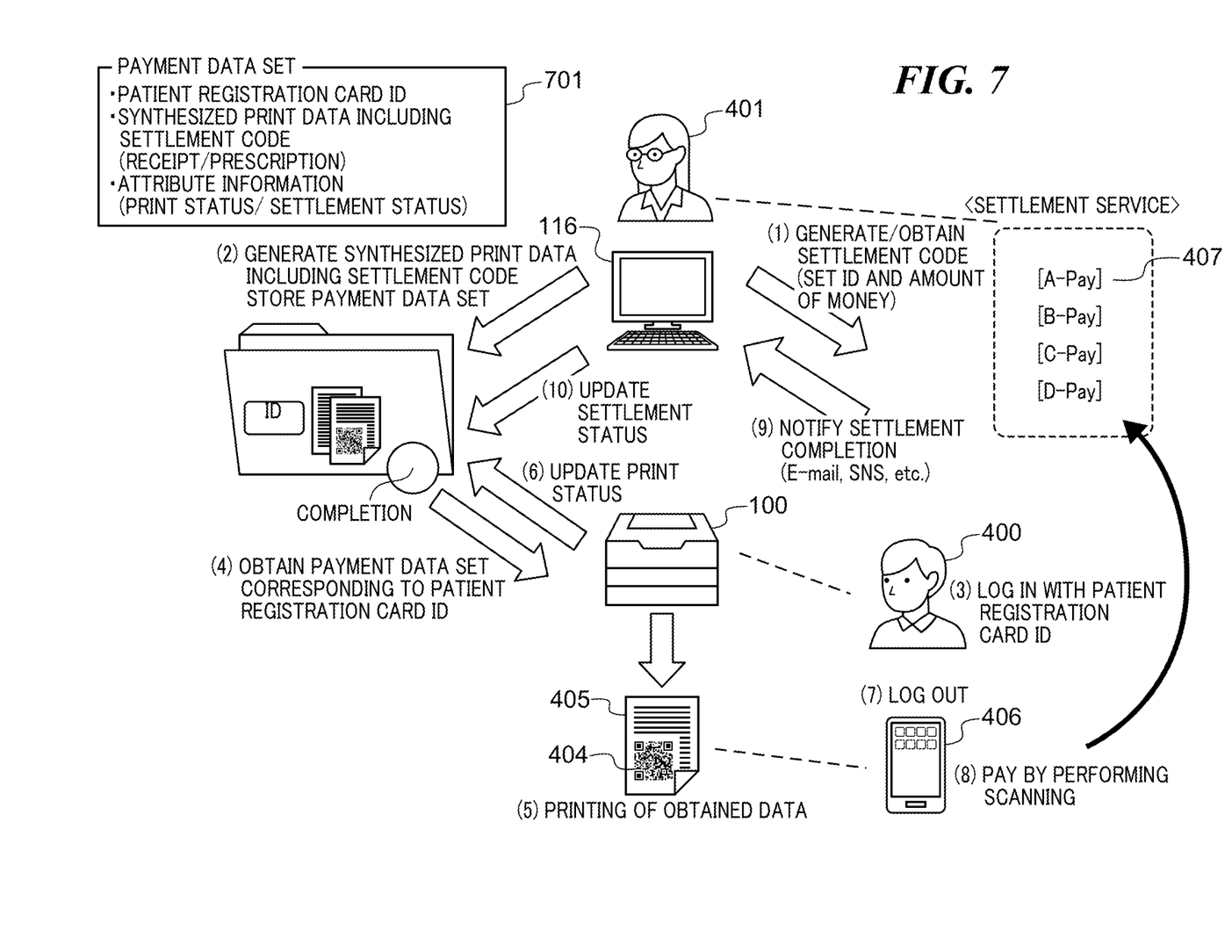
FIG. 7 is a figure for explaining detailed procedures of steps S305 to S307 in a second embodiment.

FIG. 7 is a figure for explaining detailed procedures of the steps S305 to S307 in the second embodiment. In the step S305 described above, the information processing apparatus 116 generates the print data for performing the printing of the receipts and the prescriptions according to the instruction issued by the clerical worker 401, and also accesses to the external settlement service. Here, the information processing apparatus 116 accesses to the external settlement service, which is selected together with the selected settlement method by the patient 400 in the step S301 from the plurality of external settlement services that are capable of realizing the payment by the settlement code. As with (1) in FIG. 4, the information processing apparatus 116 requests the external settlement service to generate the settlement code based on the patient registration card ID of the patient 400 and the amount of money that are inputted by the clerical worker 401 (see, for example, (1) in FIG. 7). When the information processing apparatus 116 obtains the settlement code from the external settlement service as a response to this request, the information processing apparatus 116 generates synthesized print data including settlement code. The synthesized print data including settlement code is print data obtained by synthesizing the obtained settlement code with the print data, which is designated by the clerical worker 401 together when inputting the patient registration card ID, by means of a specified format stored in the storage unit 120 in advance. Further, the information processing apparatus 116 stores a payment data set 701 that includes the synthesized print data including settlement code and the attribute information in the above predetermined storage place (see, for example, (2) in FIG. 7). After that, processes same as the processes in (3) and (4) of FIG. 4 are performed (see, for example, (3) and (4) of FIG. 7). Next, the image forming apparatus 100 refers to the attribute information that is included in the obtained payment data set 701. For example, in the case that both the print status and the settlement status in this attribute information are "unexecuted", the image forming apparatus 100 prints the synthesized print data including settlement code (see, for example, (5) in FIG. 7). As a result, the receipt 405 including the image 404 of the settlement code is outputted. After that, processes same as the processes in (6) to (10) of FIG. 4 are performed (see, for example, (6) and (10) of FIG. 7).

Figure 8:
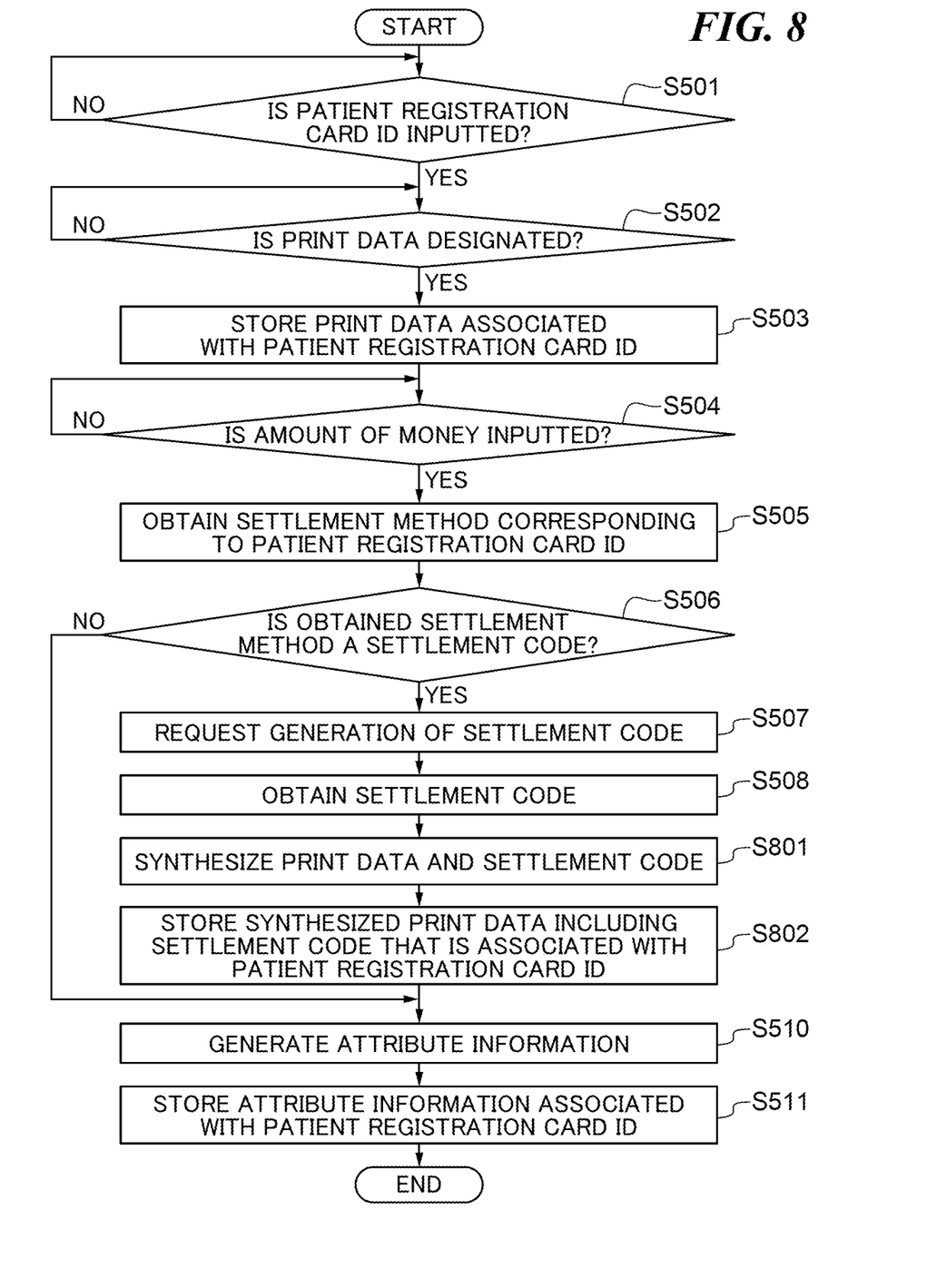
FIG. 8 is a flowchart that shows procedures of a payment data set storage processing executed by an information processing apparatus of the second embodiment.

FIG. 8 is a flowchart that shows procedures of a payment data set storage processing executed by the information processing apparatus 116 of the second embodiment. As with the payment data set storage processing of FIG. 5, the payment data set storage processing of FIG. 8 is also realized by the CPU 117 of the information processing apparatus 116 executing a program, which is read out from the ROM 118 and then is written into the RAM 119. Further, as with the payment data set storage processing of FIG. 5, the payment data set storage processing of FIG. 8 is also executed when the clerical worker prepares for the printing of the receipts and the prescriptions in the step S305.

As shown in FIG. 8, the CPU 117 performs the processing of the steps S501 to S508. Next, the CPU 117, which functions as a synthesizing unit, synthesizes the settlement code with the print data by means of the specified format stored in the storage unit 120 in advance (a step S801). As a result, the synthesized print data including settlement code is generated. Next, the CPU 117 associates the synthesized print data including settlement code with the patient registration card ID, and then stores the synthesized print data including settlement code, which is associated with the patient registration card ID, in the above predetermined storage place together with the print data before synthesizing (a step S802). Next, the CPU 117 performs the processing of the steps S510 and S511. In this way, in the present embodiment, the payment data set 701 that includes the synthesized print data including settlement code, which is associated with the patient registration card ID, is stored in the predetermined storage place.

Figure 9:
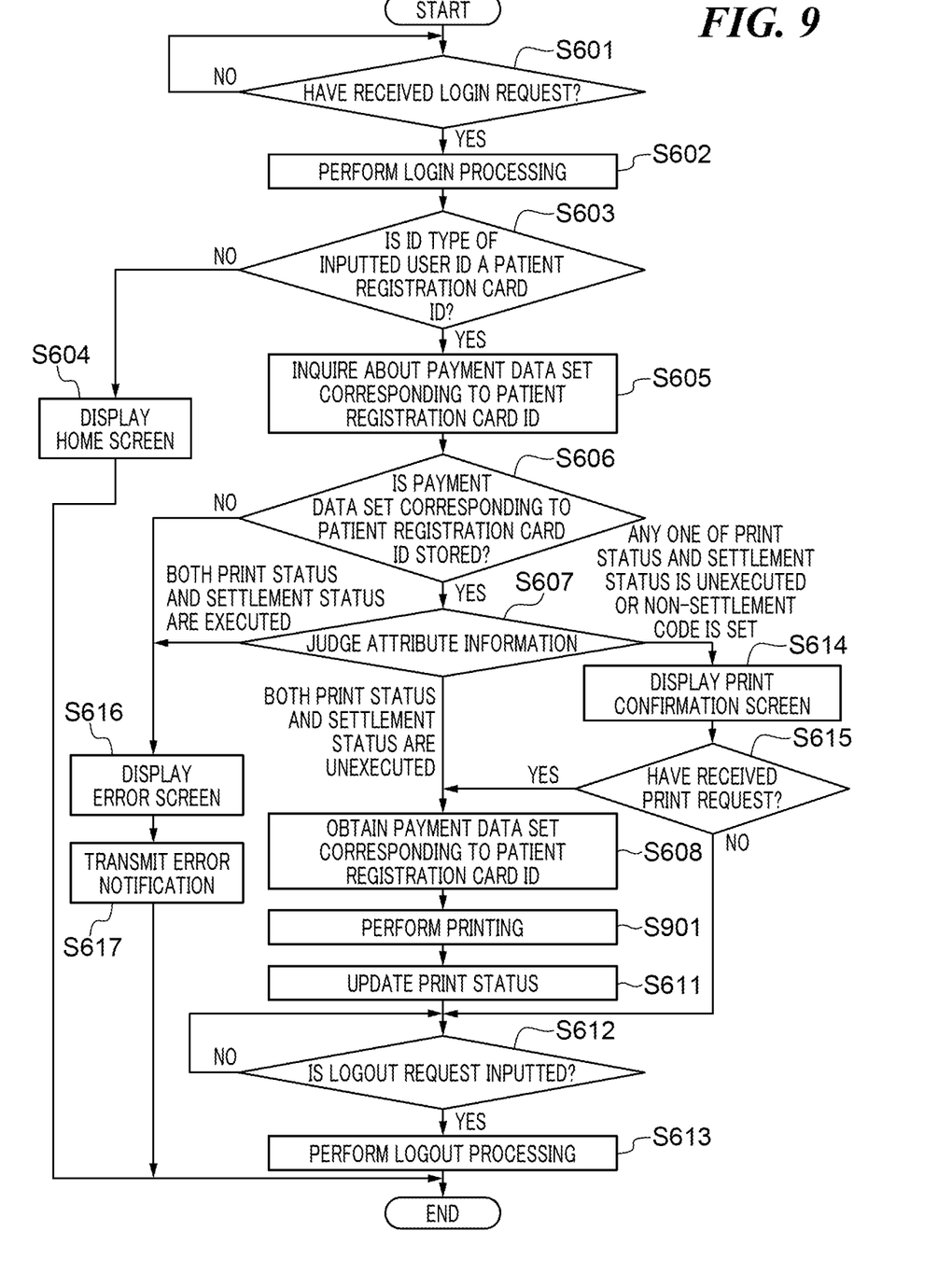
FIG. 9 is a flowchart that shows procedures of a print control processing executed by an image forming apparatus of the second embodiment.

FIG. 9 is a flowchart that shows procedures of a print control processing executed by the image forming apparatus 100 of the second embodiment. As with the print control processing of FIG. 6, the print control processing of FIG. 9 is also realized by the CPU 102 of the image forming apparatus 100 executing a program, which is read out from the ROM 103 or the storage memory 105 and then is written into the RAM 104. Further, as with the print control processing of FIG. 6, the print control processing of FIG. 9 is also executed when the patient performs the printing of the print data and the settlement code in the step S306.

As shown in FIG. 9, the CPU 102 performs the processing of the steps S601 to S607.

In the step S607, in the case that any one of the print status and the settlement status in the above attribute information is "unexecuted", or in the case that the non-settlement code is set in the said settlement status, the print control processing proceeds to the step S614. Further, the processing of the step S614 and following is the same as the flowchart of FIG. 6.

In the step S607, in the case that both the print status and the settlement status in the above attribute information are "executed", the print control processing proceeds to the step S616. Further, the processing of the step S616 and following is the same as the flowchart of FIG. 6.

In the step S607, in the case that both the print status and the settlement status in the attribute information, which is included in the response notification received from the external apparatus, are "unexecuted", the print control processing proceeds to the step S608. The payment data set obtained by the CPU 102 in the step S608 includes the synthesized print data including settlement code that is generated in the step S801. Next, the CPU 102 controls the printer unit 115 to perform printing of the synthesized print data including settlement code (a step S901). Next, the CPU 102 performs the processing of the step S611 and following.

In the above-described embodiment, the settlement code for settling the amount of money, which is inputted together when inputting the patient registration card ID, is obtained from the external settlement service, and the synthesized print data including settlement code, in which the said settlement code is synthesized, is associated with the patient registration card ID and then is stored. As a result, it is possible to certainly associate the print data with the settlement code provided by the external settlement service.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2020-174021, filed Oct. 15, 2020, which is hereby incorporated by reference herein in its entirety.

What is claimed is:

1. A system comprising:
at least one processor that causes the system to:
transmit information for generating a code used for paying an amount of money to an external settlement service;
receive the code generated based on the transmitted information;
synthesize the received code and print data;
cause a printer to execute printing based on data generated through synthesization of the received code and the print data;
judge whether or not payment of the amount of money using the code has been completed; and
notify an error in a case that it has been judged that the payment of the amount of money using the code has been completed.

2. The system according to claim 1, wherein the at least one processor further causes the system to:
judge whether or not both the printing executed by the printer and the payment of the amount of money using the code have been completed; and
notify an error in a case that it has been judged that both the printing and the payment of the amount of money using the code have been completed.

3. The system according to claim 1, wherein the at least one processor further causes the system to:
accept identification information, and
synthesize a code, which is received and corresponds to the accepted identification information, and the print data.

4. The system according to claim 3, wherein the identification information is a user ID.

5. The system according to claim 1, wherein the code is a two-dimensional code.

6. A control method for a system, the control method comprising:
a transmitting step of transmitting information for generating a code used for paying an amount of money to an external settlement service;
a receiving step of receiving the code generated based on the information transmitted in the transmitting step;
a synthesizing step of synthesizing the code received in the receiving step and print data;
a printing step of executing printing based on data generated through synthesizing performed in the synthesizing step and the print data;
a judging step of judging whether or not payment of the amount of money using the code has been completed; and
a notifying step of notifying an error in a case that it has been judged in the judging step that the payment of the amount of money using the code has been completed.

7. A non-transitory computer-readable storage medium storing a program for causing a computer to execute a control method for a system, the control method comprising:
a transmitting step of transmitting information for generating a code used for paying an amount of money to an external settlement service;
a receiving step of receiving the code generated based on the information transmitted in the transmitting step;
a synthesizing step of synthesizing the code received in the receiving step and print data;
a printing step of executing printing based on data generated through synthesizing performed in the synthesizing step;
a judging step of judging whether or not payment of the amount of money using the code has been completed; and
a notifying step of notifying an error in a case that it has been judged in the judging step that the payment of the amount of money using the code has been completed.

* * * * *